United States Patent [19]
Carlson et al.

[11] Patent Number: 5,562,812
[45] Date of Patent: Oct. 8, 1996

[54] FREE FLOW ELECTROPHORESIS DEVICE FOR BIOMOLECULE PURIFICATION AND SEPARATION IN ZERO AND ONE G

[75] Inventors: Alfred Carlson; Lee D. Coraor; Norman S. Deno, all of State College; Wayne R. Pauley, Lemont; Brock Spigelmyer, Yeagertown; Frederick Mensch, Millheim; Raymond Kristofik, Julian; Andrew J. Harned, State College, all of Pa.

[73] Assignee: The Penn State Research Foundation, University Park, Pa.

[21] Appl. No.: 415,873

[22] Filed: Apr. 3, 1995

[51] Int. Cl.[6] .................................................. B01D 61/42
[52] U.S. Cl. ........................... 204/600; 204/645; 204/549
[58] Field of Search .................................. 204/600, 645, 204/549

[56] References Cited

U.S. PATENT DOCUMENTS

| | | | |
|---|---|---|---|
| 3,821,102 | 6/1974 | Fletcher et al. | 204/299 |
| 3,980,631 | 9/1976 | Prochazka et al. | 260/112.5 R |
| 3,989,612 | 11/1976 | Kragt et al. | 204/180 G |
| 4,046,877 | 9/1977 | White et al. | 424/177 |
| 4,181,589 | 1/1980 | Brooks | 204/180 R |
| 4,309,268 | 1/1982 | Richman | 204/301 |
| 4,310,408 | 1/1982 | Rose et al. | 204/301 |
| 4,359,415 | 11/1982 | Sloane | 260/112 R |
| 4,383,905 | 5/1983 | Richman | 204/180 R |
| 4,394,246 | 7/1983 | Richman et al. | 204/301 |
| 4,440,638 | 4/1984 | Judy et al. | 210/198.2 |
| 4,465,582 | 8/1984 | Richman | 204/299 R |
| 4,482,486 | 11/1984 | Brtnik et al. | 260/112.5 R |
| 4,508,645 | 4/1985 | Simek et al. | 260/112.5 R |
| 4,621,055 | 11/1986 | Theurer | 435/69 |
| 4,698,142 | 10/1987 | Muroi et al. | 204/182.3 |
| 4,729,823 | 3/1988 | Guevara, Jr. | 204/299 R |
| 4,749,458 | 6/1988 | Muroi et al. | 204/182.3 |
| 4,769,223 | 9/1988 | Volesky et al. | 423/27 |
| 4,822,250 | 4/1989 | Tsubouchi et al. | 417/45 |
| 4,897,169 | 1/1990 | Bier et al. | 204/183.2 |
| 4,900,421 | 2/1990 | Grutzner et al. | 204/299 R |
| 5,076,943 | 12/1991 | Rakow | 210/808 |
| 5,082,541 | 1/1992 | Watson | 204/180.1 |
| 5,122,246 | 6/1992 | Schmidt et al. | 204/180.1 |
| 5,131,994 | 7/1992 | Shmidt et al. | 204/180.1 |
| 5,139,680 | 8/1992 | Tarnopolsky | 210/656 |
| 5,180,480 | 1/1993 | Manz | 204/299 R |
| 5,275,706 | 1/1994 | Weber | 204/180.1 |
| 5,277,774 | 1/1994 | Shmidt et al. | 204/180.1 |
| 5,439,571 | 8/1995 | Sammons et al. | 204/180.1 |

OTHER PUBLICATIONS

*Electrokinetics in Microgravity*, RAMSES, A Facility for IML 2, 14 pages, Jul. 1989.

Primary Examiner—John Niebling
Assistant Examiner—Arun S. Phasge
Attorney, Agent, or Firm—Thomas J. Monahan

[57] ABSTRACT

An electrophoresis device is disclosed which may be partially disassembled and sterilized in an autoclave. The device includes a base and support framework extending from the base. A separation column including a separation chamber having a pair of plates spaced from and positioned generally parallel to one another is supported from the framework. A pump is provided for pumping buffer solution through the separation chamber. A sample injection device is located near an inlet of the separation chamber and a collection assembly is located near the outlet of the separation chamber. An electrical compartment is supported by the framework and controls the pump, injection device and collection assembly and is removably located in the electrical compartment. The separation column plates are made of a heat resistant plastic.

19 Claims, 10 Drawing Sheets

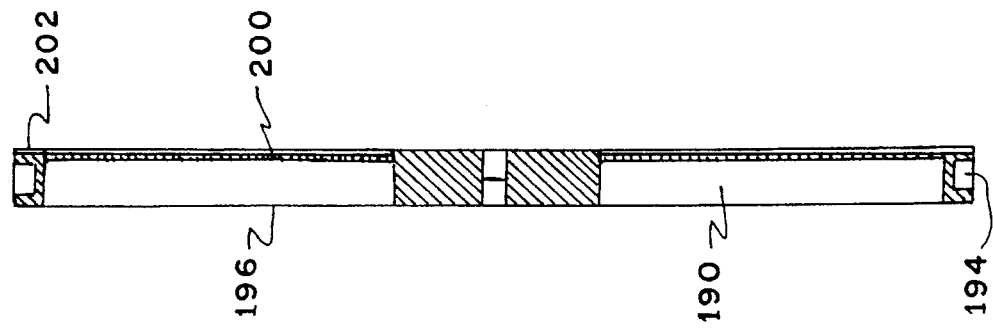
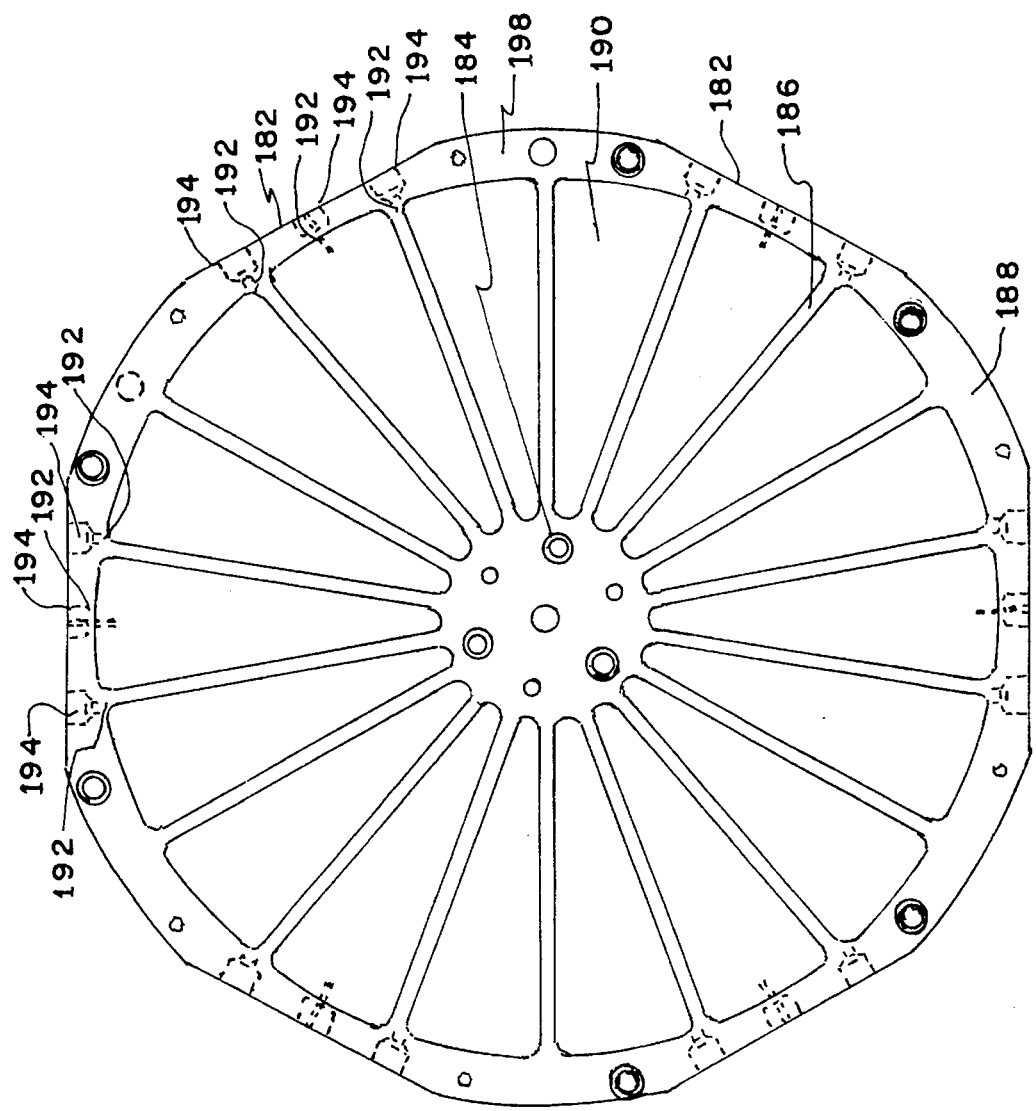

FREE FLOW ELECTROPHORESIS DEVICE FOR BIOMOLECULE PURIFICATION AND SEPARATION IN ZERO AND ONE G

Government Rights

This invention was made with Government support under Grant No. NAGW-1196 awarded by the National Aeronautics and Space Administration. The Government has certain rights in the invention.

BACKGROUND OF THE INVENTION

1. Field of the Invention

This invention relates generally to a continuous free flow electrophoresis device and, more particularly, to an easily sterilizable electrophoresis device which can be used at 0 or 1 g.

2. Description of the Prior Art

Free flow electrophoresis is a process in which a sample stream is introduced into a liquid buffer flow within a separation column. A fixed or varying electric field is maintained across the separation column perpendicular to the buffer flow. Species of virtually identical biomolecules often have different surface electrical charges and thus react or move differently within electric fields. Passing a selected sample of biomolecules or bioparticles through an electric field in an appropriate buffer or carrier results in the molecules migrating to separate positions in the electrical field representative of their charge. Thus, visually and chemically similar biomolecules can be separated into subspecies according to their electric charge. Individual components in the sample stream are separated from each other on the basis of their mobility in the imposed electric field and are collected at the exit of the separation column in one or several collection vessels.

Contamination of the sample and buffer has been a constant problem with conventional electrophoresis devices. To help reduce this contamination problem, investigators commonly operate conventional electrophoresis devices at about 4° C. to reduce the chances of opportunistic organism growth. However, not all separations may be desirable at this low temperature. Furthermore, large cooling systems are required to maintain these low operating temperatures. To help eliminate this contamination problem, it would be helpful to be able to sterilize the electrophoresis device. However, conventional electrophoresis devices are not generally sterilizable due to the fact that they are constructed as a single liquid flow and electrical control unit which is not easily disassembled. Further, many conventional electrophoresis devices use polycarbonate based separation plates and membranes which are subject to surface cracking, known as "crazing", when subjected to typical sterilization temperatures of about 250° F.

With the advent of the space shuttle program, a need has arisen for a continuous flow electrophoresis apparatus which is capable of functioning in the gravity free environment of space as well as in a ground based laboratory. Due to the duration of space shuttle flights, an onboard electrophoresis device, and in particular the buffer flow loop, would need to be sterilized prior to flight to prevent contamination and biological growth occurring in the device during extended space flight. Therefore, a continuous flow electrophoresis device for use in space should be easily sterilizable by conventional means, such as autoclaving. Typical autoclaves operate at 250° F. Hence, the electrophoresis device should be capable of withstanding this sterilization atmosphere for at least 35 minutes to achieve complete sterilization. This sterilization capability would also be useful for terrestrial use of an electrophoresis device by allowing rapid sterilization of the device between runs of toxic or infectious samples and by significantly lowering the possibility of contamination from undesirable organisms or their byproducts. The ability to quickly and easily sterilize the electrophoresis device would also allow separations to be conducted at elevated temperatures and would reduce the need for large and costly cooling systems.

Further, conventional electrophoresis devices rely on gravity in the collection of sample fractions. Obviously, a gravity flow collection system would be totally inadequate for space flight. Therefore, a non-gravity dependent collection system is imperative for any space flight electrophoresis apparatus.

Therefore, it is an object of the invention to provide a continuous flow electrophoresis device which may be easily partially disassembled and sterilized in an autoclave.

Further, it is an object of the present invention to provide a sample collection system capable of collecting and storing electrophoresis fractions in 0 or 1 g.

SUMMARY OF THE INVENTION

An electrophoresis device which may be partially disassembled and sterilized in an autoclave includes a base and a support framework extending therefrom. A separation column including a separation chamber defined by at least a pair of plates spaced from and positioned generally parallel to one another is supported from the framework. The separation chamber has an inlet end and an outlet end. A pump is provided for pumping buffer solution through the separation chamber from the inlet end to the outlet end. A sample injection assembly is located near the inlet end of the separation chamber and a collection assembly is located near the outlet end of the separation chamber. An electrical compartment is supported by the framework and an electrical control assembly for controlling the pump, injection assembly and collection assembly is removably located in the electrical compartment. The plates of the separation column are made of a heat resistant plastic.

The heat resistant plastic can be resistant to a temperature of about 250° F. and a steam atmosphere without developing substantial surface cracking and can be polysulfone.

At least one cooling chamber can be located adjacent, and in thermal communication with, the separation chamber and a pump can be provided for pumping buffer solution through the cooling chamber.

The electrophoresis device can include a sample injector assembly having a sample holder for removably holding a sample cartridge with a plurality of sample cavities. The sample injector assembly can further include a device for selectively withdrawing a sample from a selected sample cavity of the sample cartridge.

The pair of plates of the separation chamber can include a plurality of holes disposed along the lateral edge of each of the plates, with a heat resistant membrane disposed over the holes on each of the plates. This heat resistant membrane can be resistant to a temperature of about 250° F. and a steam atmosphere without developing substantial surface cracking, and can be polysulfone.

The collection assembly can include a collection canister including a plurality of collection plates, with each collection plate having a plurality of collection chambers disposed therein. The collection assembly can further include a needle plate having a plurality of needles disposed therein, where the needle plate is opposed to a plenum assembly having a plenum chamber. The needle plate and the plenum assembly can be configured such that the plurality of needles are slidable through the plenum chamber, with the needles in fluid communication with the separation chamber. The electrophoresis device can include a plurality of flow baffles disposed in the at least one cooling chamber.

The collection plates can include a hydrophobic membrane disposed over a first side of the collection plate to seal each of the collection chambers.

A fraction collection assembly can be provided for the electrophoresis device. The fraction collection assembly includes a needle plate having at least one needle disposed therein. The needle has a shaft with a discharge located in the shaft. The needle is in fluid communication with the separation chamber. The fraction collection assembly further includes a plenum assembly having a first side and a second side with a plenum chamber disposed therein. The needle passes through the first side of the plenum assembly and extends into the plenum chamber and the needle plate and plenum assembly are slidable from a first position to a second position. A collection canister is provided adjacent the plenum assembly. In the first position, the needle plate, plenum assembly and collection canister are configured such that the discharge of the needle is located in the plenum chamber. In the second position, the shaft of the needle passes through the second side of the plenum assembly into the collection canister such that the discharge is located in the collection canister.

The collection canister can include a plurality of collection plates, with each collection plate having a plurality of collection chambers.

At least one motor can be provided for sliding the needle plate and plenum assembly from the first position to the second position. The fraction collection assembly can include a motor for rotating the collection canister and can further include a waste conduit connecting the plenum chamber to a waste container.

A complete understanding of the invention will be obtained from the following description when taken in connection with accompanying drawing figures wherein like reference characters identify like parts throughout.

BRIEF DESCRIPTION OF THE DRAWINGS

FIG. 7 is a side, sectional view of a collection plate;

FIG. 8 is an end view of the collection plate of FIG. 7;

DESCRIPTION OF THE PREFERRED EMBODIMENT

Figure 1:
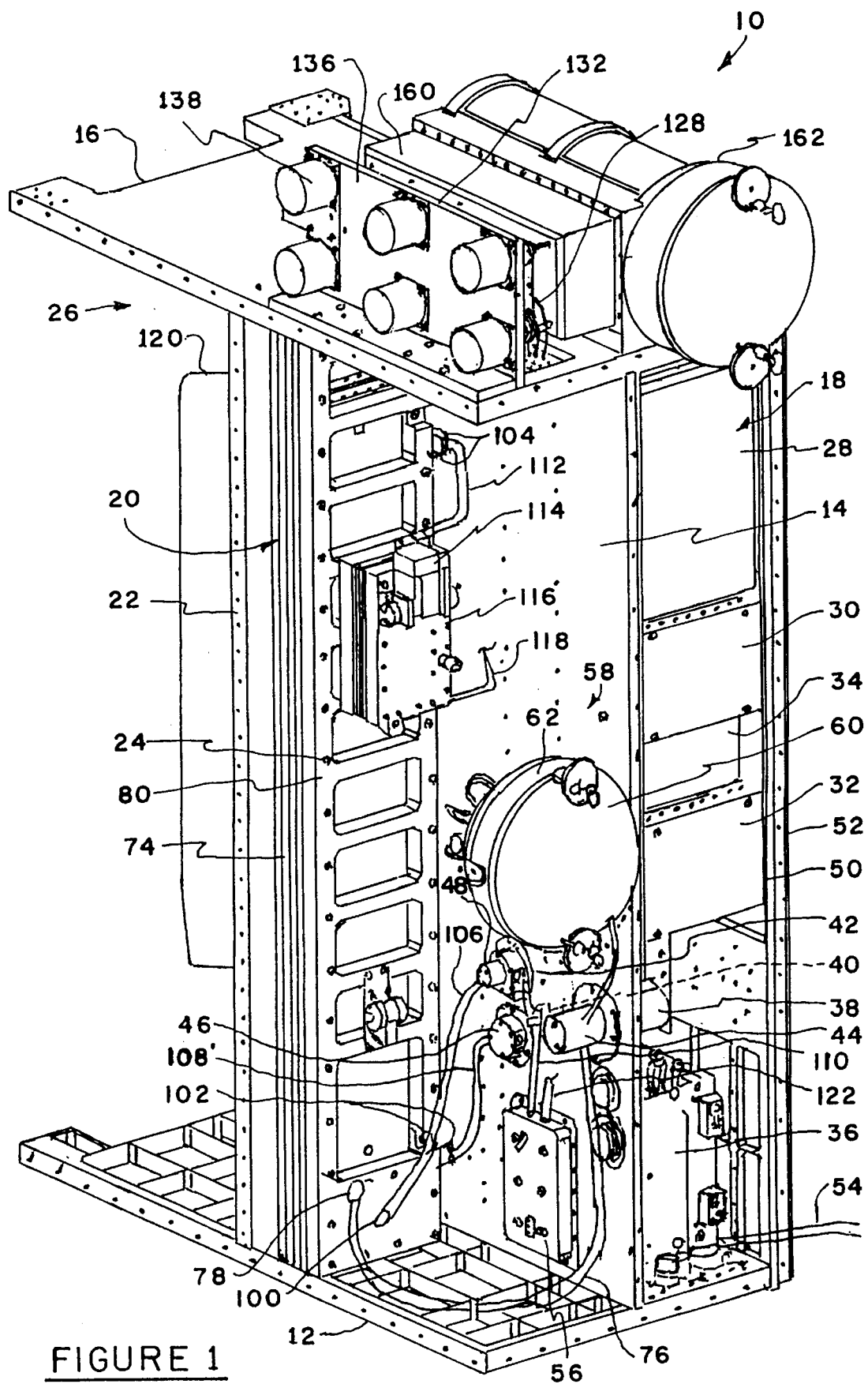
FIG. 1 is a perspective view of a continuous flow electrophoresis device.
Figure 5:
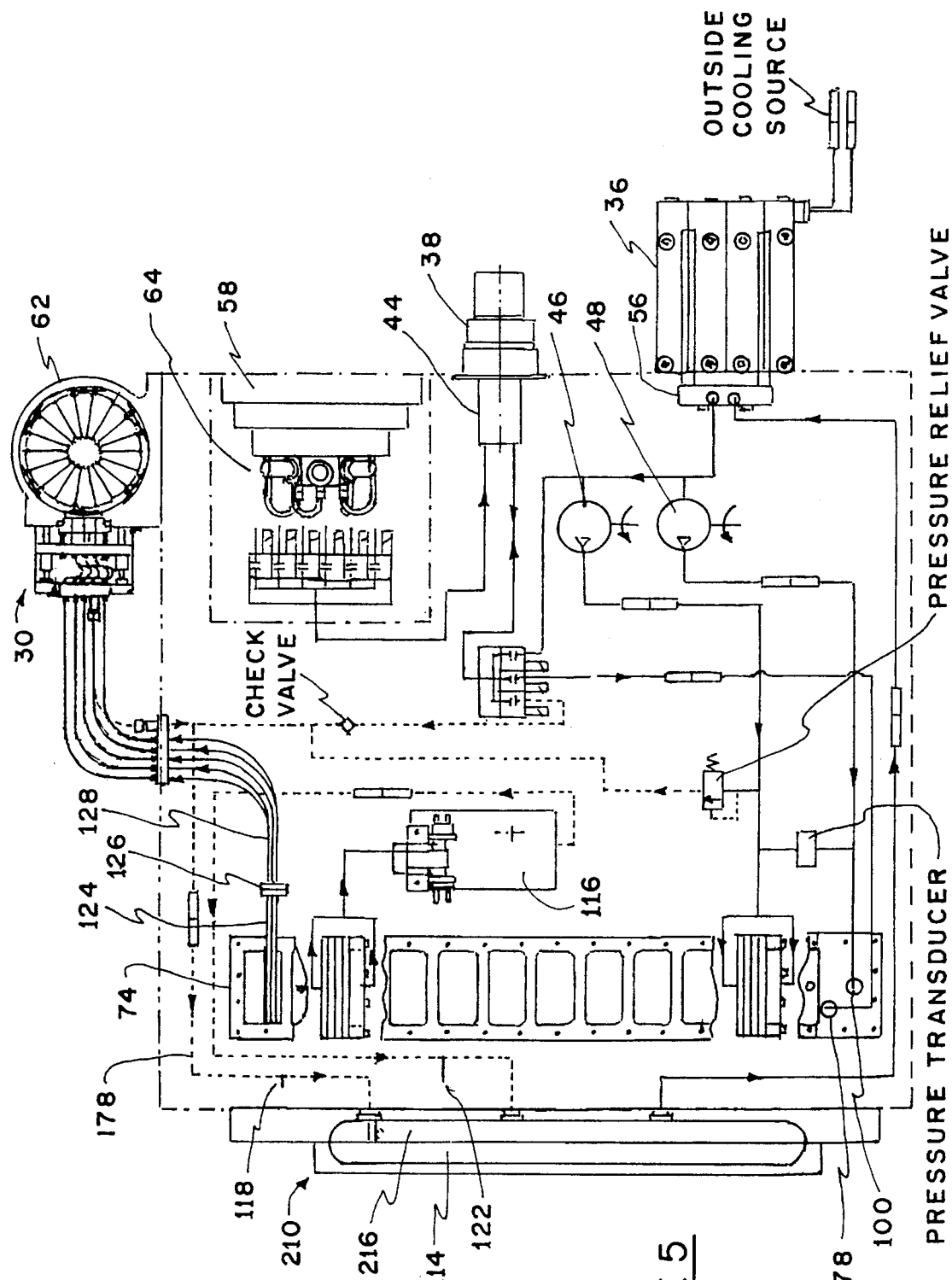
FIG. 5 is a schematic flow diagram of the electrophoresis device showing the interrelation of various functional elements.

A continuous flow electrophoresis device is generally designated 10 in FIGS. 1 and 5 of the drawings. The individual components of device 10 will first be identified and the operation of, and fluid flow through, device 10 will then be described. Electrophoresis device 10 includes a base 12 with a support framework 14 extending upwardly therefrom. A top plate 16 is attached to support framework 14 opposite base 12. Support framework 14 divides electrophoresis device 10 into two general compartments, an electrical compartment 18 and a fluid compartment 20. A lateral partition 22 further divides fluid compartment 20 into a separation column compartment 24 and a buffer tank compartment 26.

Electrical compartment 18 contains the motors, heat exchanger and electrical control elements for control of device 10. These control elements include a primary and secondary control computer 28, a control card rack 30 and a measurement card rack 32. A status display panel 34 is positioned between control card rack 30 and measurement card rack 32. A thermoelectric heat exchanger 36 is located below measurement card rack 32. Electrical compartment 18 further includes a sample pump motor 38, a cooling pump motor 40 and a separation chamber pump motor 42.

Sample pump motor 38 is mechanically coupled to a syringe-type sample pump 44 mounted on support framework 14 in fluid compartment 20. O-rings mounted on both sides of support framework 14 between sample pump motor 38 and sample pump 44 prevent fluid leakage into electrical compartment 18. Cooling pump motor 40 and separation chamber pump motor 42 are magnetically coupled to a cooling pump 46 and separation chamber pump 48, respectively, located in fluid compartment 20. Cooling pump motor 40 with cooling pump 46 and separation chamber pump motor 42 with separation chamber pump 48 are of a magnetic drive type, with completely sealed flow paths and no through shaft seals. Cooling pump 46 and separation chamber pump 48 are mounted on support framework 14 with a magnetic coupling end of each pump 46, 48 projecting into electrical compartment 18. O-ring seals are located between the respective pumps 46, 48 and motors 40, 42 which isolate fluid compartment 20 from electrical compartment 18 to prevent any leakage or electrical shock hazard. Control computer 28, control card rack 30, status display panel 34 and measurement card rack 32 are carried as a unit in an electrical rack 50 slidably mounted between support framework 14 and an outer wall 52 and are preferably EMI shielded.

Thermoelectric heat exchanger 36 is used to remove heat from buffer fluid flowing through device 10. Heat exchanger 36 includes two cooling plates and four hot plates which are hydraulically separate from the cooling plates but are connected via a heat exchange conduit 54 to an exterior cooling flow loop (not shown). Heat exchanger 36 is in fluid communication with a heat exchange reservoir 56 mounted on support framework 14 in fluid compartment 20. The control elements, motors and heat exchanger in electrical compartment 18 are in electrical communication with each other through, for example, shielded cables as are known in the art. Further, a conventional cooling fan (not shown) may be mounted in electrical compartment 18 to provide cooling air to the control elements.

Figure 12:
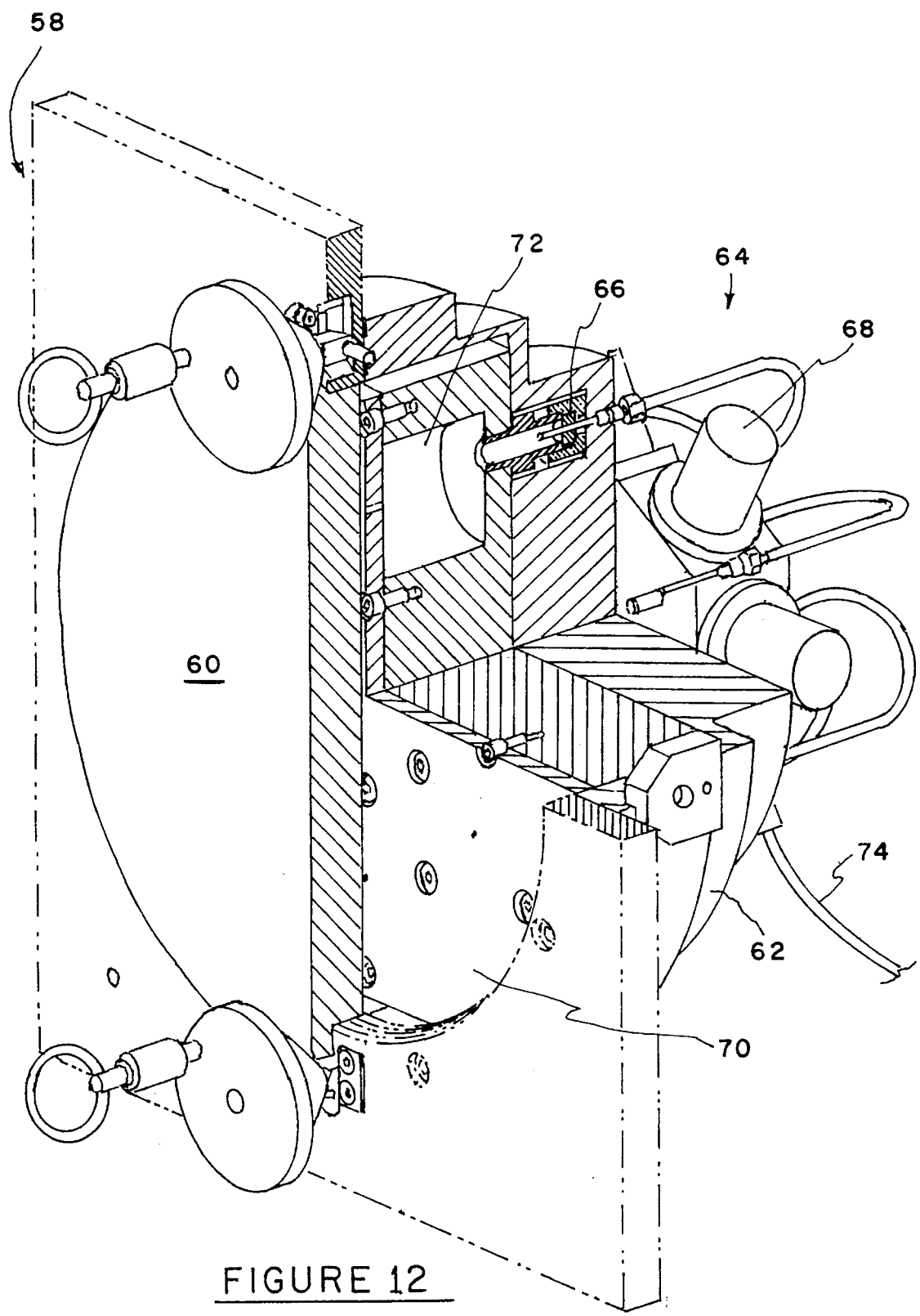
FIG. 12 is a perspective, broken away view of a sample injector assembly.

Fluid compartment 20 includes an injector cartridge housing 58, as shown in FIGS. 1 and 12. Injector cartridge housing 58 includes a door 60 mounted to a cup shaped sample holder 62. A sample withdrawal assembly 64 is mounted on the back of sample holder 62. Withdrawal assembly 64 includes six solenoid controlled withdrawal needles 66, each withdrawal needle 66 having an associated solenoid valve assembly 68 in electrical communication with the electrical control elements in electrical compartment 18. A sample cartridge 70 having at least one, and preferably six, sample cavities 72 may be removably mounted in injector cartridge housing 58. A sample conduit 75 connects withdrawal assembly 64 to sample pump 44. Sample pump 44 is further connected to a separation column 74 by a sample injection conduit 76 connected to a sample injection port 78 located at the base of separation column 74.

Figure 3:
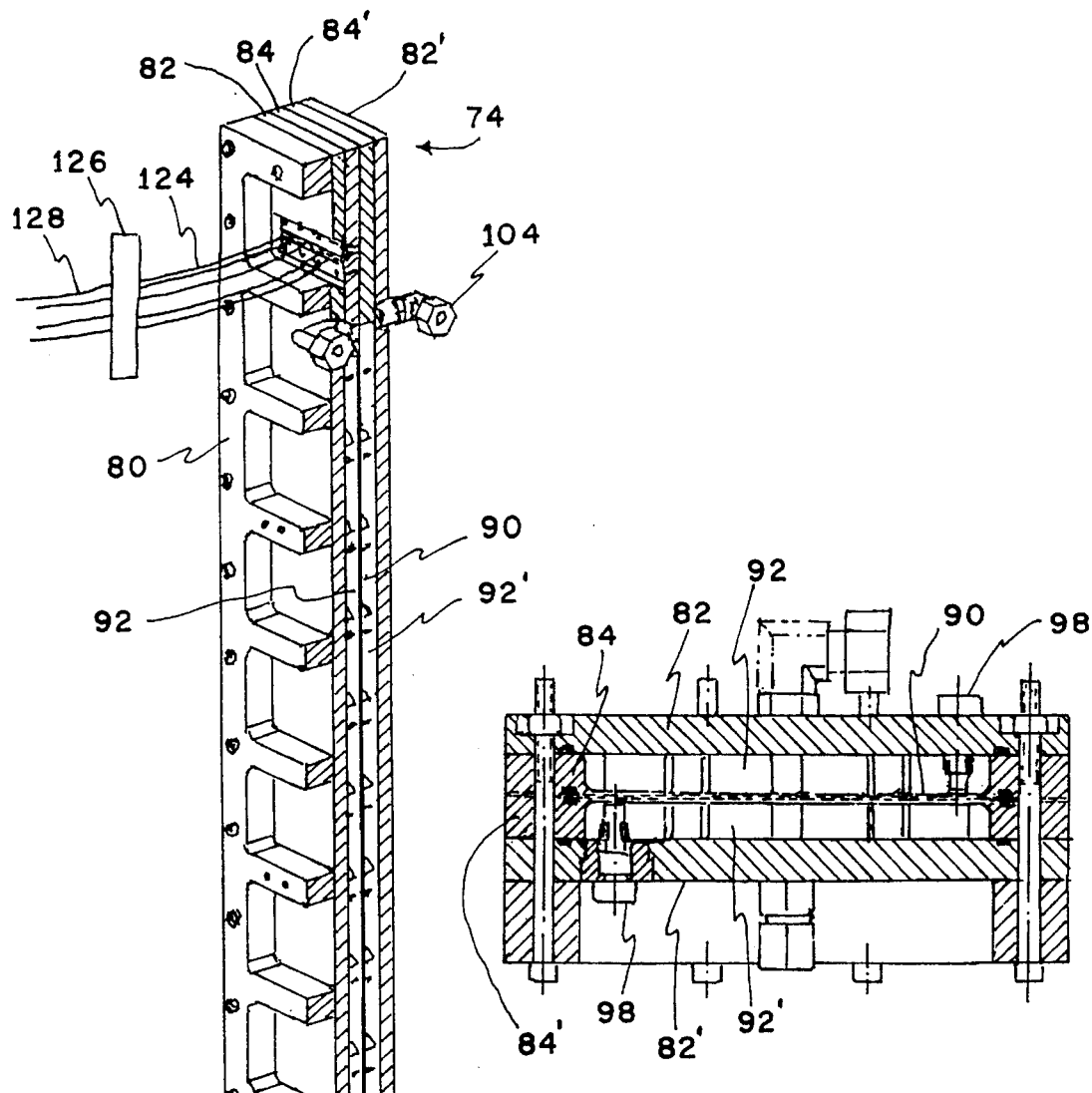
FIG. 3 is a plan, sectional view of the column shown in FIG. 2.
Figure 2:
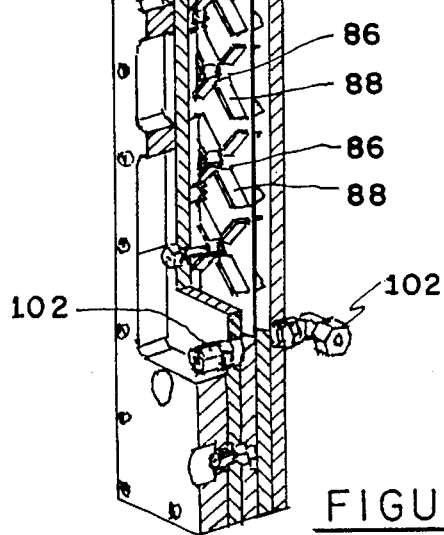
FIG. 2 is a cut away sectional view in perspective of a separation column of the device shown in FIG. 1.

As shown in FIGS. 1–4, separation column 74 includes an aluminum ladder 80 supporting four heat resistant plastic (for example, polysulfone) plates. Outer plates 82 and 82' surround a pair of inner plates 84 and 84'. As shown in FIGS. 2 and 3, outer plates 82 and 82' are substantially rectangular while inner plates 84 and 84' have a central, longitudinal depression machined therein. A series of X-shaped flow baffles 86 formed by rectangular fins 88 are carried on inner plates 84 and 84'. The inner and outer plates are arranged as shown in FIGS. 2 and 3 such that a separation chamber 90 is formed by a gap located between adjacent inner plates 84 and 84'. A pair of cooling chambers 92 and 92' are formed between outer plates 82 and 82' and inner plates 84 and 84' with flow baffles 86 located in cooling chambers 92 and 92'. Inner plates 84 and 84' and outer plates 82 and 82' are bonded together, for example, by a heat resistant adhesive and are then bolted to aluminum ladder 80 as shown in FIG. 2. Separation chamber 90 is in thermal communication with cooling chambers 92 and 92'.

Figure 4:
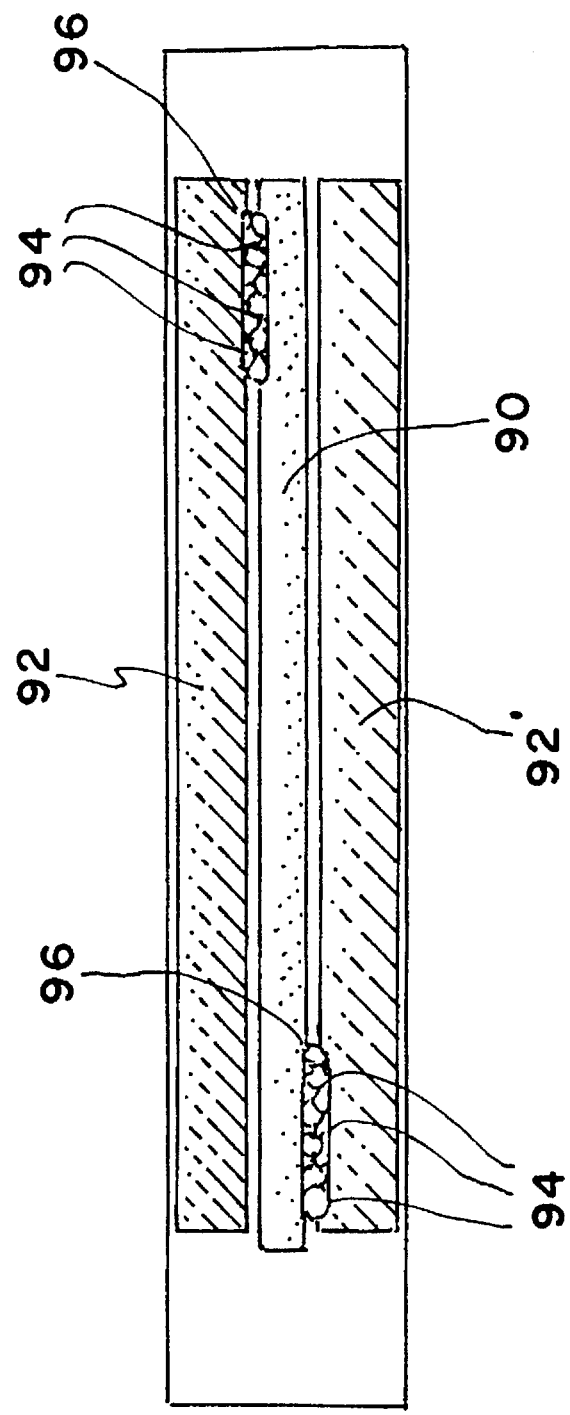
FIG. 4 is a detailed sectional view of the separation column.

As shown in FIGS. 3 and 4, there is a series of small holes 94 machined along one lateral edge of each inner plate 84 and 84' such that holes 94 of one inner plate are on an opposite side of separation chamber 90 than holes 94 of the other inner plate. These holes 94 are covered by a heat resistant plastic, for example polysulfone, membrane 96 which prevents fluid flow between cooling chambers 92 and 92' and separation chambers 90, but allows ion flow. Platinum electrodes 98 are placed in the cooling chambers, one acting as a cathode in one cooling chamber and the other acting as an anode in the other cooling chamber. Electrodes 98 extend along the length of separation column 74.

Figure 10:
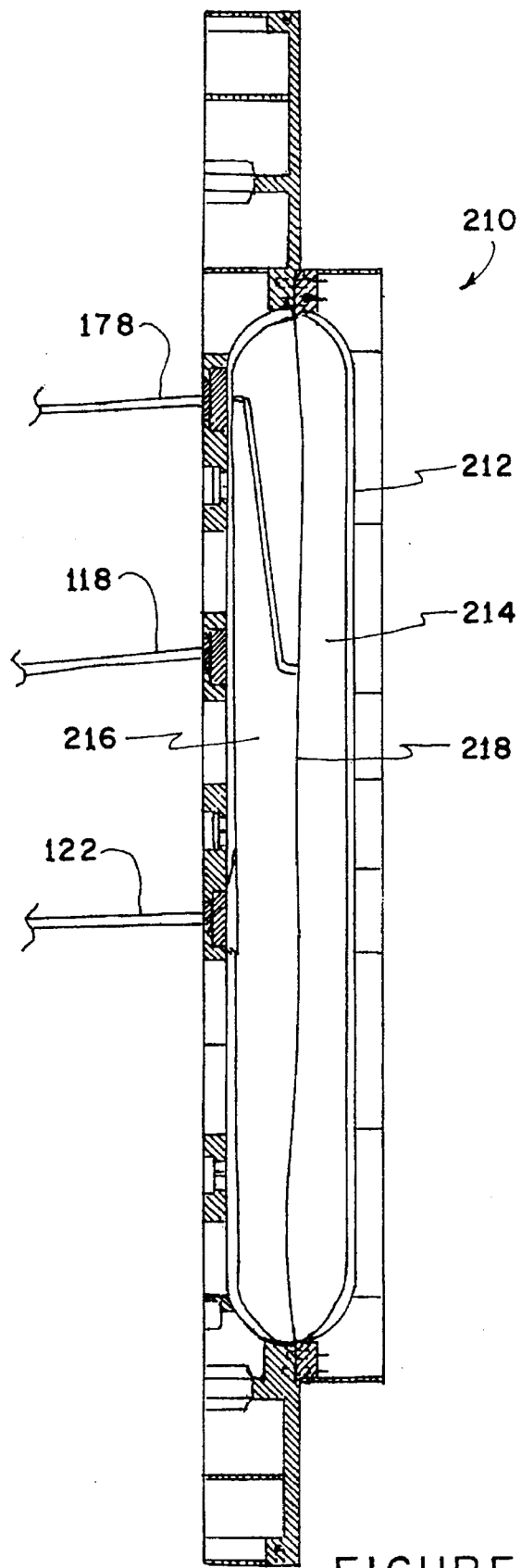
FIG. 10 is a side, sectional view of a buffer tank assembly of the electrophoresis device.

The bottom of separation column 74 further includes a separation chamber inlet 100 and a pair of cooling chamber inlets 102 (See FIG. 1). A pair of cooling chamber outlets 104 is located near the top of separation column 74. Separation chamber inlet 100 is connected to separation chamber pump 42 by a conduit 106. Cooling chamber inlets 102 are connected via a conduit 108 to cooling pump 46. Separation chamber pump 48 and cooling pump 46 are both connected to heat exchange reservoir 56 by a branched conduit 110. Cooling chamber outlets 104 are connected via a conduit 112 to a vacuum pump 114 and degasser assembly 116. A discharge conduit 118 connects degasser assembly 116 with a buffer tank assembly 120 in buffer tank compartment 26, as shown in FIG. 10. Buffer tank assembly 120 is also connected to reservoir 56 by a supply conduit 122. The connection between buffer tank compartment 26 and separation chamber compartment 24 will be discussed in detail hereinafter.

As indicated in FIGS. 2 and 5, many (for example, ninety-nine) separate Teflon connection tubes 124 are positioned across the top of separation chamber 90, with each collection tube 124 separated from an adjacent collection tube by a distance of approximately 0.050 inch. For ground use, these collection tubes 124 may be directly connected to a conventional collector system wherein each tube is located above a separate sample collector vessel, for example a test tube, and discharge from each collection tube 124 flows into a separate test tube. However, for use in space, a non-gravity dependent collection system is required. In the non-gravity dependent collection system, collection tubes 124 are connected to a collection manifold 126. Ninety-nine manifold tubes 128, corresponding to the ninety-nine collection tubes 124 pass through top plate 16 and are connected between collection manifold 126 and a fraction collection assembly 130.

Figure 6:
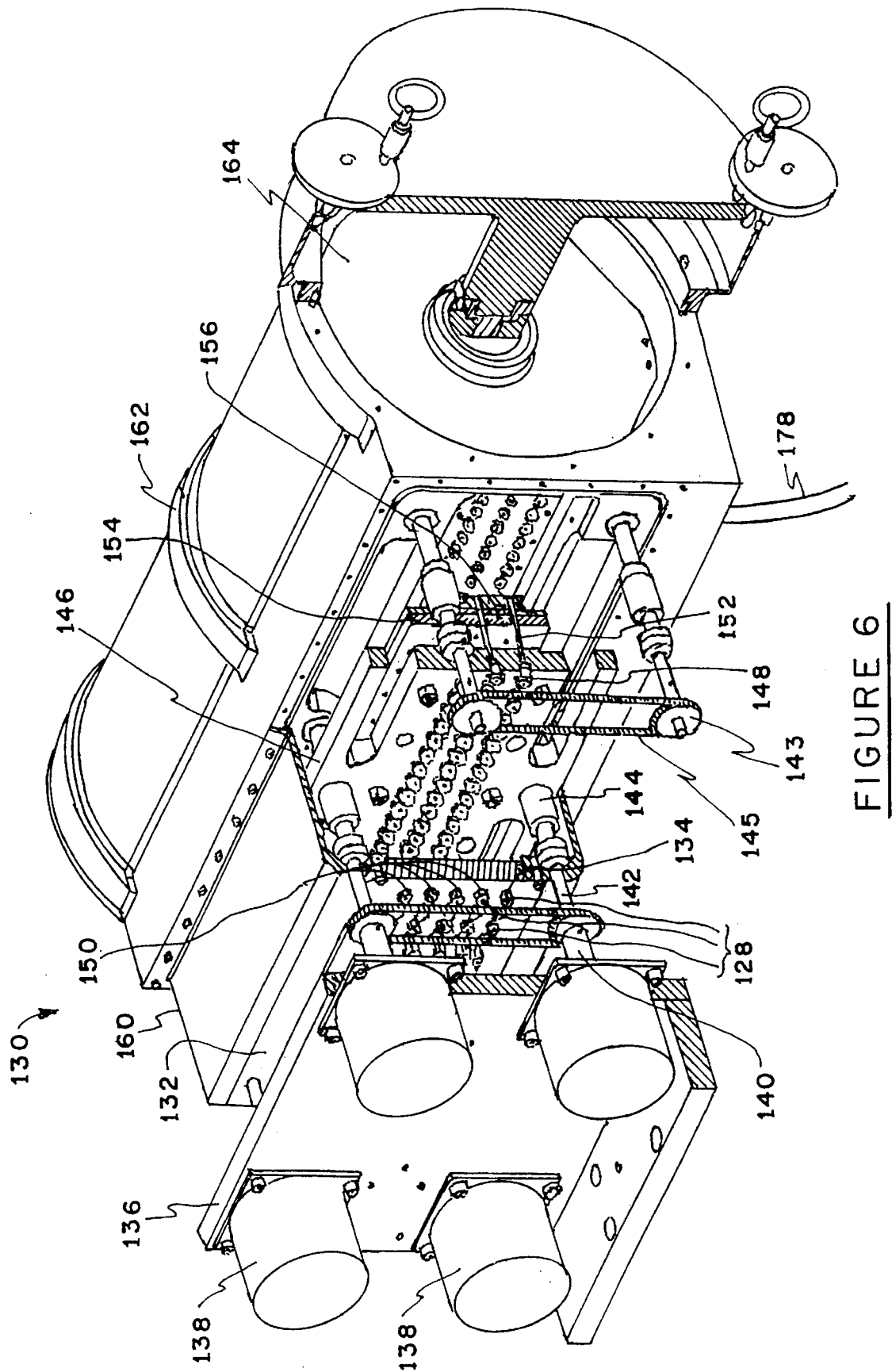
FIG. 6 is a broken away, perspective view of a fraction collection assembly.

As shown in FIGS. 1 and 6, fraction collection assembly 130 includes a connection plate 132 having ninety-nine connection couplings 134 to which the ninety-nine manifold tubes 128 are connected. A drive motor support 136 is removably fastened to top plate 16 adjacent connection plate 132 and supports at least one, for example six, drive motors 138. Each drive motor 138 is connected via a removable coupling 140 to a shaft 142 which passes through connection plate 132 and is connected to a drive screw assembly 144 connected to a needle plate 146. Each shaft 142 carries a gear element 143. Drive motors 138 are arranged in an over/under relationship as shown in FIG. 6 with gear elements 143 of each pair of drive motors 138 connected by a flexible belt 145.

Figure 11B:
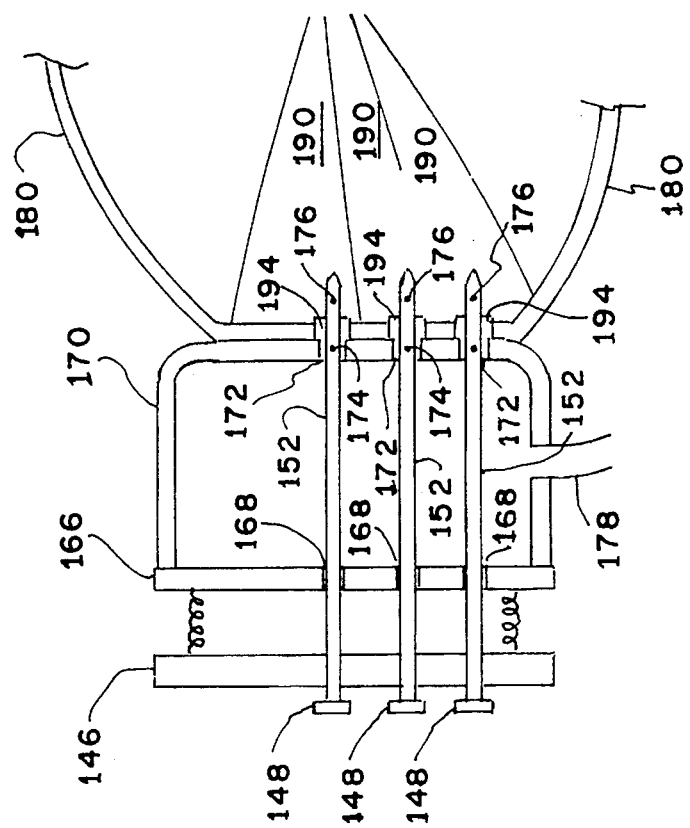
FIGS. 11A and 11B are side, sectional views of a needle plate and plenum assembly.
Figure 11A:
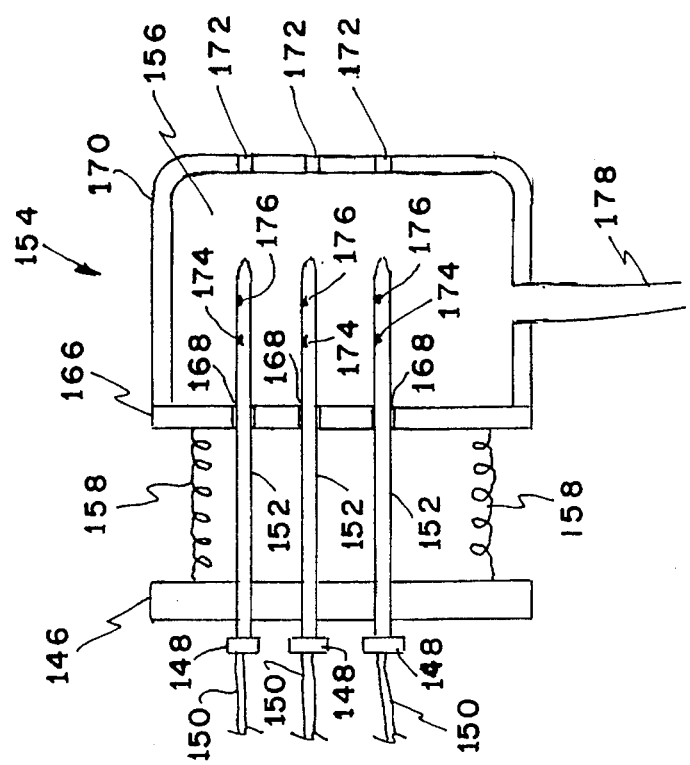

Needle plate 146 carries three rows of stainless steel needles 148 with each row having thirty-three needles 148 located therein. Flexible conduits 150 connect each connection coupling 134 to a needle 148. As shown in FIGS. 6, 11A and 11B, each needle 148 includes a shaft 152 which passes through a plenum assembly 154 having a plenum chamber 156. Plenum assembly 154 is spaced from needle plate 146 by springs 158. Needle plate 146 and plenum assembly 154 are slidably housed in a needle plate housing 160. Needle plate housing 160 is adjacent to a collector housing 162 having a rotatable collection canister 164 disposed therein.

As shown in FIG. 11A, plenum assembly 154 includes a planar, upright wall 166 with ninety-nine sealing elements 168 through which shafts 152 of needles 148 pass. A curved side wall 170 is attached to upright wall 166 by conventional means, for example by welding, to form plenum chamber 156. Side wall 170 also has sealing elements 172 positioned opposite sealing elements 168 of upright wall 166. As shown in FIG. 11A, each needle shaft 152 has two apertures 174 and 176 spaced apart from each other. The end of each needle 148 is sealed so flow from needles 148 can only occur through apertures 174 and 176. A waste line 178 is connected between plenum chamber 156 and buffer tank compartment 26, as will be described in detail hereinafter.

Figure 9:
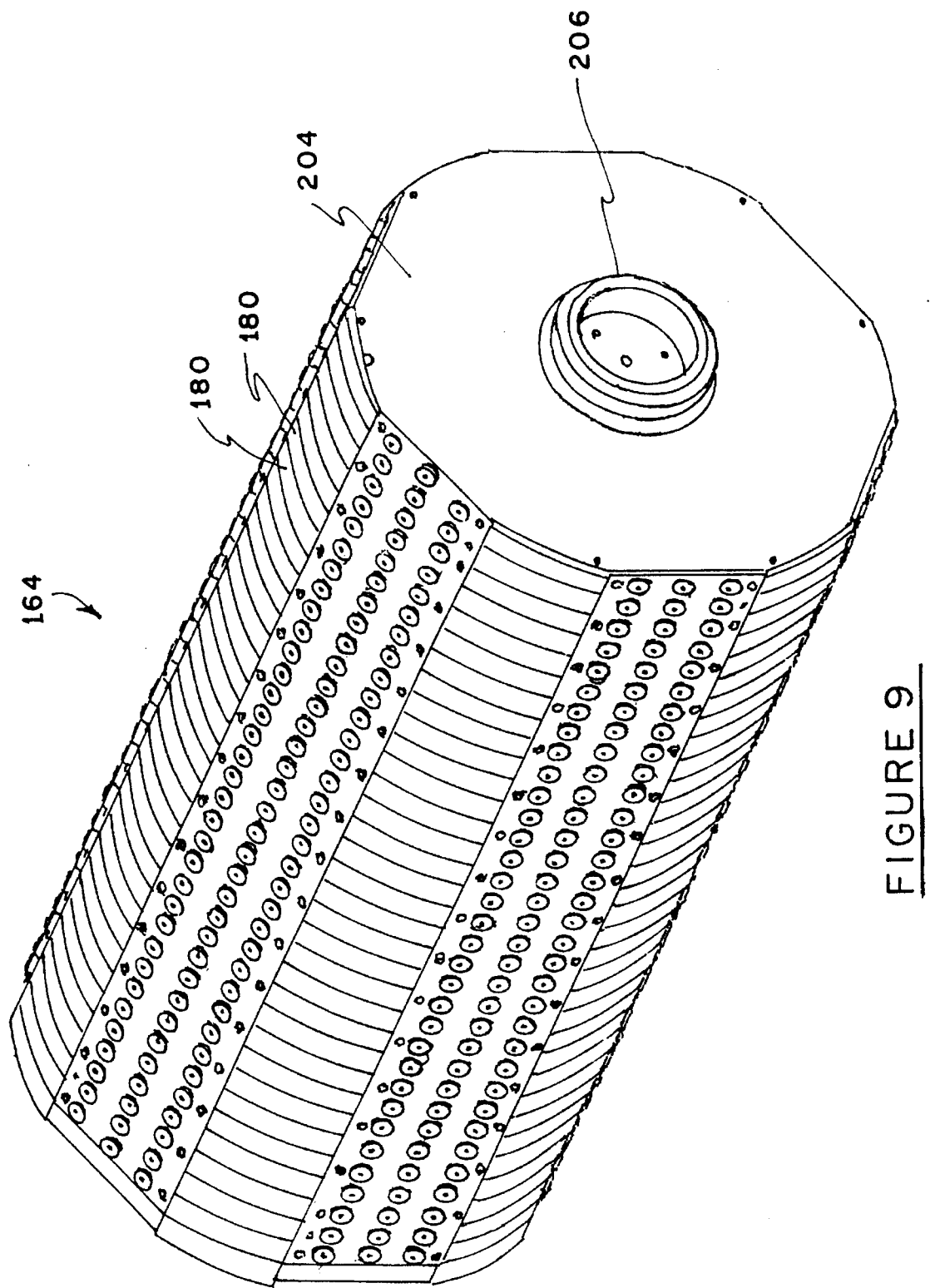
FIG. 9 is a perspective view of a collection canister.

As shown in FIG. 9, collection canister 164 includes a plurality of collection plates 180, shown in FIGS. 7 and 8. Each collection plate 180 is substantially circular but has six flattened areas 182 located on the circumference of collection plate 180. Each collection plate 180 has a central hub 184 with a plurality of ribs 186 extending from hub 184 to a circumferential ridge 188 dividing plate 180 into eighteen individual collection chambers 190. Each flattened area 182 includes three ejection ports 192 each leading to a separate collection chamber 190. Each ejection port 124 includes a sealing element 194.

A hydrophobic membrane 196 is bonded to a first side 198 of plate 180 to seal collection chambers 190. A plurality, for example thirty-three, individual collection plates 180 are then connected side-to-side as shown in FIG. 9 with flattened areas 182 of adjacent plates 180 aligned. As shown in FIG. 8, a second side 200 of each plate 180 is slightly recessed from circumferential ridge 188 and an air vent 202 is machined through the outer edge of circumferential ridge 188 into this recess. As shown in FIG. 6, thirty-three individual collection plates 180 are aligned with first side 198 of one plate 180 adjacent second side 200 of adjacent plate 180 to form collection canister 164. Each plate 180 is aligned such that flattened areas 182 on adjacent plates 180 are aligned as shown in FIG. 6. A pair of end caps 204, each having a bearing surface 206, are attached at opposite ends of collection canister 164. Collection canister 164 is then rotatably mounted in collector housing 162. Collector housing 162 includes a door 208 for easy access and removal of collection canister 164 from collector housing 162.

As shown in FIG. 10, buffer tank compartment 26 includes a buffer tank assembly 210. Buffer tank assembly 210 includes a buffer tank bag 212 separated into a waste buffer bag 214 and a sterile buffer bag 216 by a dividing membrane 218. Waste line 178 from plenum chamber 156 passes into buffer tank assembly 210 and through sterile buffer bag 216 into waste buffer bag 214. Discharge conduit 118 from degasser assembly 116 is connected to sterile buffer bag 216. Supply conduit 122 connects sterile buffer bag 216 to reservoir 56.

OPERATION

Operation of electrophoresis device 10 will now be described. Initially, sterile buffer bag 216 is filled with sterile buffer solution. Sterile buffer solution flows from sterile buffer bag 216 through conduit 122 into reservoir 56 where the buffer solution is cooled under the influence of heat exchanger 36. The buffer solution exits reservoir 56 through branched conduit 110 and is supplied to both separation chamber pump 48 and cooling pump 46. Thus, the sterile buffer solution is used as both the sample transport medium and the cooling medium.

First, flow from cooling pump 46 will be described. Cooled buffer solution flows from cooling pump 46 at about 1200 cc/min through conduit 108 into cooling chamber inlets 102 at the base of separation column 74. Buffer solution flows upward through cooling chambers 92 and 92' and through flow baffles 86. Baffles 86 are configured to cause individual buffer flows through cooling chambers 92 and 92' to cross and mix as the buffer flows through the column, thus promoting improved heat exchange between separation chamber 90 and cooling chambers 92 and 92' and preventing temperature gradients from forming in the cooling chambers.

Buffer from cooling chambers 92 and 92' exits the top of separation column 74 through cooling chamber outlets 104. The buffer solution then flows through conduit 112, under the influence of vacuum pump 114, into degassing assembly 116 where gases are removed from the cooling buffer liquid. The buffer then flows through conduit 118 back into sterile buffer bag 216 for recirculation through electrophoresis device 10.

Buffer flow from separation chamber pump 48 will now be described. Buffer solution from separation chamber pump 48 flows at about 100 cc/min through conduit 106 into separation chamber inlet 100. Buffer solution then flows upwards through separation chamber 90. Upon command from the electrical control elements, withdrawal assembly 64 draws a sample from one sample cavity 72 in sample cartridge 70. The selected sample flows through conduit 75, sample pump 44 injection port 78 and is injected into the buffer flow in separation chamber 90. The sample flows upwardly through separation chamber 90 where, under the influence of the electric field created by electrodes 98, separation of differently charged molecules or particles occurs across the width of separation chamber 90. Buffer solution containing the separated sample exits the top of separation chamber 90 through the ninety-nine spaced collection tubes 124. The collected fraction samples then pass through collection manifold 126, through manifold tubes 128 and into connection couplings 134 on connection plate 132. Flexible conduits 150 allow flow from each connection coupling 132 to a designated needle 148 on needle plate 146.

Depending on whether electrophoresis device 10 is in a "sample collection mode" or "waste mode" determines how buffer flow proceeds from this point. Looking first at the waste flow mode, FIG. 11A shows positioning of needle 148 in plenum assembly 154 during the waste mode. Buffer solution from separation chamber 90 flows through flexible conduits 150 into needles 148 and out apertures 174 and 176 on needle shaft 152. Since plenum chamber 156 is a sealed chamber, this buffer flow is forced out waste line 178 by pressure into waste buffer bag 114. No gravitational forces are needed.

However, when a fraction sample is desired to be collected, collection canister 164 is rotated by a motor in electrical communication with electrical compartment 18 such that each collection plate 180 is aligned with sealing elements 194 on each flattened area 182 being aligned with sealing elements 172 of side wall 170, as shown in FIG. 11B. Drive motors 138 are activated which push needle plate 146 and plenum assembly 154 toward collection canister 164 until plenum assembly 154 abuts flat surface 182 on collection plate 180. Needle plate 146 continues to advance forcing needle shafts 152 through sealing elements 172, sealing elements 194 and into the interiors of collection chambers 190. In this collection position, each aperture 176 is located inside a collection chamber 190 while each aperture 174 is closed off in a sealing element 172. In this configuration, buffer and sample fraction flow through shafts 152 and out of apertures 176 into collection chambers 190.

As buffer and sample fraction flow into collection chamber 190, air is forced from collection chamber 190 through hydrophobic membrane 196. This air flows into the recess on second side 200 of the adjacent collection plate 180 and then passes through air vents 202 into the interior of collector housing 162. When sample collection is complete, drive motors 138 reverse pulling needle plate 146 away from upright wall 166 thus pulling each needle 148 back into the waste mode as shown in FIG. 11A to flush out the system before processing the next selected sample. Collection canister 164 is then rotated 60° to align the next set of collection chambers 190 in position for filling with the next set of sample fractions.

Because of the construction of the electrophoresis device 10, the device is not dependent upon gravity to assist in sample fraction collection and is also easily autoclavable, as will be next described. To autoclave electrophoresis device 10, electrical rack 50 is disconnected and slid out of electrical compartment 18. Sample pump motor 38, cooling pump motor 40, separation chamber pump motor 42 and drive motor support 136 are removed along with thermal electric heat exchanger 36. It is preferred that vacuum pump 114 also be removed. Separation column 74 and fluid connections are flushed and the remainder of electrophoresis device 10 is placed in an autoclave for sterilization. A preferred sterilization procedure is to autoclave electrophoresis device 10 at 250° F. for at least 35 minutes. Heat transferred through the walls of separation column 74 will raise the temperature inside to 250° F. Because the separation column plates and membrane 96 are made of heat resistant plastic, preferably polysulfone, no surface cracking or "crazing" will occur in the plates or membrane 96 during sterilization. After sterilization, the removed electrical equipment and motors can be easily and quickly replaced. Thus sterilized, the electrophoresis device 10 will remain in a sterile condition for an extended time until needed for use. After the next use, electrophoresis device 10 can then be quickly disassembled and re-sterilized in the same manner as set forth above.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and any and all equivalents thereof.

We claim:

1. An electrophoresis device which may be partially disassembled and sterilized in an autoclave, comprising:
   a base and a support framework extending therefrom;
   a separation column including a separation chamber defined by at least a pair of plates spaced from and positioned generally parallel to one another supported from said framework, said separation chamber having an inlet end and an outlet end;
   means for pumping buffer solution through said separation chamber from the inlet end to the outlet end;
   a sample injection means located near the inlet end of said separation chamber and a collection means near the outlet end of said separation chamber;
   an electrical compartment supported by said framework; and
   electrical means for controlling said pumping means, injection means and collection means, wherein said electrical controlling means is removably located in said electrical compartment; and
   wherein said separation column plates are made of a heat resistant plastic.

2. The electrophoresis device as claimed in claim 1, wherein said heat resistant plastic is resistant to a temperature of about 250° F. and a steam atmosphere without developing substantial surface cracking.

3. The electrophoresis device as claimed in claim 1, wherein said heat resistant plastic is polysulfone.

4. The electrophoresis device as claimed in claim 1, further including at least one cooling chamber adjacent and in thermal communication with said separation chamber and means for pumping buffer solution through said at least one cooling chamber.

5. The electrophoresis device as claimed in claim 4, wherein said at least one cooling chamber further includes a plurality of flow baffles disposed therein.

6. The electrophoresis device as claimed in claim 1, wherein said sample injector means includes a sample holder for removably holding a sample cartridge having a plurality of sample cavities, and wherein said sample injector assembly further includes means for selectively withdrawing a sample from a selected sample cavity of said sample cartridge.

7. The electrophoresis device as claimed in claim 1, wherein each of said pair of plates of said separation chamber includes a plurality of holes disposed along a lateral edge of each of said plates and a heat resistant membrane disposed over said holes on each of said plates.

8. The electrophoresis device as claimed in claim 7, wherein said heat resistant membrane is resistant to a temperature of about 250° F. and a steam atmosphere without developing substantial surface cracking.

9. The electrophoresis device as claimed in claim 7, wherein said heat resistant membrane is polysulfone.

10. The electrophoresis device as claimed in claim 1, wherein said collection means further includes a collection canister including a plurality of collection plates, each collection plate having a plurality of collection chambers disposed therein.

11. The electrophoresis device as claimed in claim 10, wherein said collection means further includes a needle plate having a plurality of needles disposed therein.

12. The electrophoresis device as claimed in claim 10, wherein each said collection plate further includes a hydrophobic membrane disposed over a first side of said collection plate to seal each said collection chamber.

13. The electrophoresis device as claimed in claim 10, wherein said needle has a shaft with a closed, pointed end and two spaced apart apertures disposed in said shaft.

14. The electrophoresis device as claimed in claim 1, wherein said collection means further includes a needle plate having a plurality of needles disposed therein, wherein said needle plate is opposed to a plenum assembly having a plenum chamber, and wherein said needle plate and said plenum assembly are configured such that said plurality of needles are slidable through said plenum chamber, and wherein said needles are in fluid communication with said separation chamber.

15. A fraction collection assembly for an electrophoresis device having a separation chamber, said collection assembly comprising:
    a needle plate having at least one needle disposed therein, wherein said needle has a shaft with a discharge located therein and wherein said needle is in fluid communication with said separation chamber;
    a plenum assembly having a first side and a second side and a plenum chamber disposed therein, wherein said needle passes through said first side of said plenum assembly and extends into said plenum chamber, and wherein said needle plate and said plenum assembly are slidable from a first position to a second position; and
    a collection canister adjacent said plenum assembly, wherein in said first position, said needle plate, plenum assembly and collection canister are configured such that said discharge of said needle is located in said plenum chamber and wherein in said second position, said shaft of said needle passes through said second side of said plenum assembly into said collection canister such that said discharge is located in said collection canister.

16. A fraction collection assembly as claimed in claim 15, wherein said collection canister includes a plurality of collection plates and wherein each collection plate includes a plurality of collection chambers.

17. A fraction collection assembly as claimed in claim 15, further including at least one motor for sliding said needle plate and plenum assembly from said first position to said second position.

18. A fraction collection assembly as claimed in claim 15, further including means for rotating said collection canister.

19. A fraction collection assembly as claimed in claim 15, further including a waste conduit connecting said plenum chamber to a waste container.

* * * * *